United States Patent [19]

Hewett

[11] Patent Number: 5,110,724
[45] Date of Patent: May 5, 1992

[54] MULTI-ANALYTE ASSAY DEVICE

[75] Inventor: Gary E. Hewett, Atherton, Calif.

[73] Assignee: Cholestech Corporation, Hayward, Calif.

[21] Appl. No.: 503,371

[22] Filed: Apr. 2, 1990

[51] Int. Cl.⁵ .................... C12Q 1/60; G01N 21/11
[52] U.S. Cl. .......................... 435/11; 435/14; 435/15; 435/18; 435/19; 435/25; 435/28; 435/288; 435/289; 435/291; 435/808; 422/56; 422/58; 422/100
[58] Field of Search ............. 210/651, 500.36, 500.21, 210/506, 927; 436/169, 170, 177, 178; 422/56, 57, 58, 66, 67, 111, 100; 435/805, 7, 11, 288, 289, 291, 808, 25, 28, 19, 15, 14, 18

[56] References Cited

U.S. PATENT DOCUMENTS

| 3,607,093 | 0/0000 | Stone . |
| 3,791,933 | 2/1974 | Moyer et al. . |
| 3,907,642 | 9/1975 | Richmond . |
| 3,907,645 | 9/1975 | Richmond . |
| 3,925,164 | 12/1975 | Beaucamp et al. . |
| 3,983,005 | 9/1976 | Goodhue et al. . |
| 4,038,485 | 7/1977 | Johnston et al. . |
| 4,069,017 | 1/1978 | Wu et al. . |
| 4,144,129 | 3/1979 | Gruber et al. . |
| 4,144,306 | 3/1979 | Figueras . |
| 4,181,575 | 1/1980 | Gruber et al. . |
| 4,186,251 | 1/1980 | Tarbutton . |
| 4,212,938 | 7/1980 | Gruber et al. . |
| 4,256,693 | 3/1981 | Kondo et al. . |
| 4,477,575 | 10/1984 | Vogel et al. ........................ 436/170 |
| 4,503,144 | 3/1985 | Deeg et al. . |
| 4,544,630 | 2/1985 | Ziegenhorn et al. . |
| 4,680,259 | 7/1987 | Cumbo et al. . |
| 4,816,224 | 3/1989 | Vogel et al. . |
| 4,820,489 | 4/1989 | Rothe et al. . |
| 4,826,721 | 5/1989 | Arai et al. . |
| 4,839,296 | 6/1989 | Kennedy et al. ..................... 436/170 |
| 4,849,340 | 7/1989 | Oberhardt ............................ 422/110 |
| 4,855,108 | 8/1989 | Masuda et al. ........................ 422/56 |
| 4,877,586 | 10/1989 | Devaney, Jr. et al. ................ 422/58 |
| 4,987,085 | 1/1991 | Allen et al. ........................... 422/56 |

FOREIGN PATENT DOCUMENTS 0229982 12/1985 European Pat. Off. .

Primary Examiner—Jill A. Johnston
Assistant Examiner—Jan M. Ludlow
Attorney, Agent, or Firm—Peter J. Dehlinger; Carol A. Stratford

[57] ABSTRACT

An assay device for assaying multiple analytes in a drop-size blood sample. The device includes a sample dispenser designed to distribute a small-volume blood sample to multiple transfer sites, by capillary flow of the blood sample through sieving and distributing matrices which separate blood cells from serum as the sample fluid migrates toward the transfer sites. A test plate in the device carries multiple absorbent test pads, each containing reagent components for use in detection of a selected analyte. The test plate is mounted on the dispenser for movement toward and away from a transfer position at which the exposed surface regions of the pads are in contact with associated sample-transfer sites, for simultaneous transfer of sample fluid from such sites to the pads in the support.

16 Claims, 2 Drawing Sheets

MULTI-ANALYTE ASSAY DEVICE

This application is a continuation-in-part of U.S. patent application for "Controlled-Volume Assay Method and Apparatus," Ser. No. 320,474, filed Mar. 8, 1989 is pending.

1. Field of the Invention

The present invention relates to device for performing multiple analyte tests on a small-volume blood sample.

2. Background of the Invention

Assays for detecting the presence and levels of a variety of analytes in body fluid samples are known. Such assays are often designed for simplicity of use so that they can be reliably conducted in a doctor's office or other clinical setting where personnel may have little training in clinical assay procedure or in interpreting assay results. Typically, such assays involve a one-step assay procedure, or employ automated or semi-automated procedures, with the assay reading being determined from a reaction end-point.

One type of diagnostic assay format which is generally amenable to simple, one-step assays is an absorptive-pad device, containing a pad or matrix designed to absorb a sample volume, and to produce an analyte-dependent chemical reaction which can be detected on the pad's surface. Examples of absorptive-pad assay devices and methods include U.S. Pat. Nos. 3,983,005, 4,069,017, 4,144,306 and 4,447,575.

A number of factors have heretofore limited the accuracy of assays which are based on a conventional reaction matrix or pad format. One limitation is the variable amount of detectable reaction product formed in the presence of a given amount of analyte, due to variations in the stability of the reagents in the pad, variations in temperature and other reaction conditions, as well as the presence of variable amounts of interfering compounds in the analyte-containing sample.

These sources of variability have been largely eliminated in a three-pad self-corrected assay system and method in which analyte concentration is determined from a standard curve, and corrected for interference based on the measured signal product readings from the three pads. The assay system is described in co-owned U.S. patent application for "Self-Corrected Assay Method and System," Ser. No. 238,775 filed Aug. 30, 1988.

Another source of inaccuracy in determining analyte concentration by conventional reaction-pad assays stems from variations in sample volume in a test pad. In particular, if an absorbent reaction pad is allowed to take up a liquid sample by surface wetting, it will tend to overfill, i.e., continue to fill even after complete wetting of the pad has occurred. The overfilling produces a surface film on the pad which may alter the reflectance or absorption characteristics of the pad, and thus skew the surface reading used to determine total analyte-dependent product formed in the reaction. The greater volume of sample in the pad will also increase uncertainty in the final analyte concentration.

Increasingly, it is desirable in analyte testing to test for a battery of different analytes, particularly in testing serum lipid levels, such as cholesterol, cholesterol subfractions, and triglycerides. Further, blood testing procedures are greatly simplified if the blood sample used for testing is a drop of blood, rather than a larger blood sample obtained by needle and syringe (which requires trained medical personnel) and which typically involves additional handling to separate blood serum or plasma from blood cells.

In summary, what is desired, but has heretofore not been attained, is a simple dry-pad sample assay device which (a) is designed for multiple analyte assays, (b) employs a single drop of whole blood, typically less than 50 $\mu$l as sample, as the test material, and (c) provides a controlled sample volume delivery to multiple absorption assay pads.

3. Summary of the Invention

It is one general object of the invention to provide an absorption-pad assay device for performing multiple analyte tests on a small-volume blood sample.

It is a more specific object of the invention to provide such a device for use in testing multiple blood analytes, using a single drop of blood of 50 $\mu$l or less as the test sample.

It is another specific object of the invention to provide such a device in which substantially the same amount of sample material is taken up into multiple absorbent assay pads.

The assay device of the invention includes a sample dispenser having a support, and a sieving matrix on the support which functions as a chromatography medium to retard blood cells of a blood sample being drawn through the matrix by capillary flow. Downstream of the sieving matrix is a second capillary-flow matrix which distributes the sample to multiple sample-transfer sites. The total absorption volume of the two matrices is preferably less than 50 $\mu$l. Residual blood cells remaining in the blood fluid sample after passage through the first matrix are removed upstream of the sample-transfer sites by (i) migration through the second matrix and/or (ii) a microporous membrane interposed between the two matrices.

A test plate in the device carries a plurality of wettable, absorbent assay pads, each having an exposed surface region and containing reagents for reacting with a selected analyte, when sample fluid is transferred to the pad, for analyte detection. The plate is mounted on the sample dispenser for movement toward and away from a sample-transfer position at which the surface regions of the pads are in contact with associated sample-transfer sites, for simultaneous transfer of cell-free sample fluid from the transfer sites to the assay pads.

In one embodiment, for use in assaying serum cholesterol and lipoproteins, the test plate includes first, second, and third pads, each of which includes, as assay reagents, a peroxidase and a dye which is converted in the presence of $H_2O_2$ to a detectable signal reaction product. The reagents in the pads further include:

(i) in the first pad, a known amount of a reference compound which is not present in the blood sample, and a reference-compound oxidase effective to generate $H_2O_2$ by reaction with the reference compound, (ii) in the second pad, cholesterol esterase and cholesterol oxidase enzymes, and (iii) in the third pad, triglyceride hydrolase, L-glycerol kinase, and L-glycerol-3-phosphate oxidase.

The reference compound is preferably a D-amino acid, and the reference-compound oxidase is D-amino acid oxidase. For use in assaying free and esterified serum cholesterol, the above lipid-assay device further includes a fourth pad having the same reagent components as the second pad, except for cholesterol esterase, which is absent in the fourth pad.

The device is designed particularly for use in a controlled-volume assay apparatus which operates to (a) move the test plate in the apparatus to its sample-transfer position, (b) control the time during which the device is maintained in its sample-transfer position, and (c) move the test assay pads out of contact with the sample-transfer sites after a selected transfer period. The assay apparatus is described in parent U.S. patent application for "Controlled-Volume Assay Method and Apparatus," Ser. No. 320,474, filed Mar. 8, 1989.

These and other objects and features of the invention will become more fully apparent when the following detailed description of the invention is read in conjunction with the accompanying drawings.

DETAILED DESCRIPTION OF THE INVENTION

A. Assay Device

Figure 1:
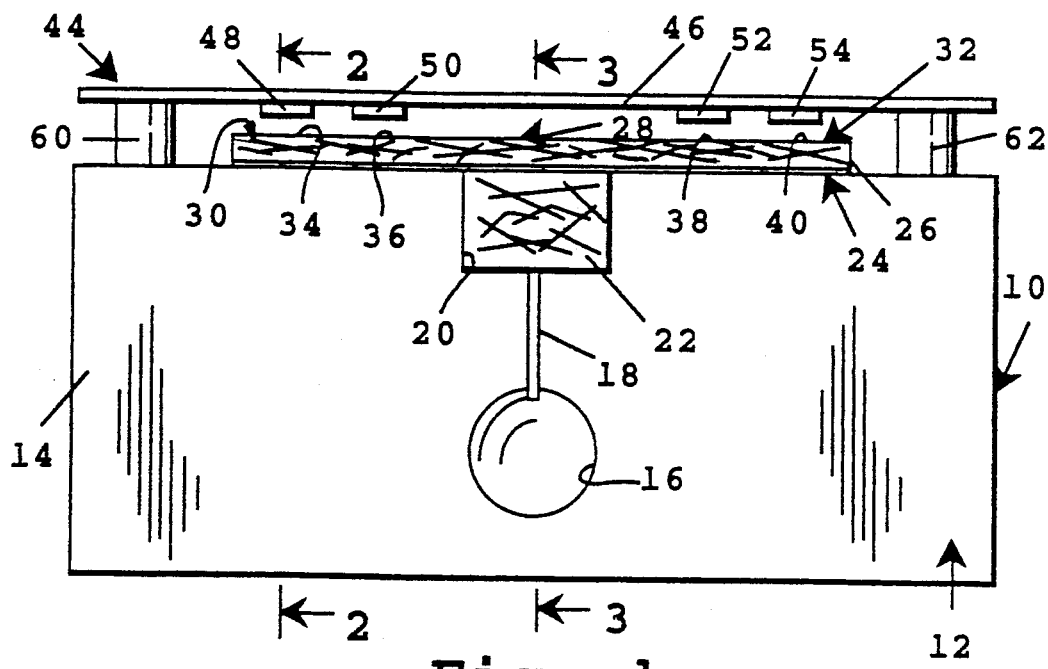
FIG. 1 is a plan view of a sample-delivery device constructed according to the invention.
Figure 2:
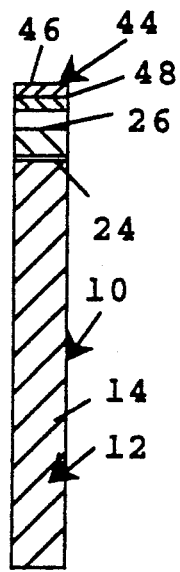
FIG. 2 is a sectional view taken along line 2—2 of FIG. 1.

FIGS. 1-4 illustrate a sample delivery device 10 constructed according to the invention. A sample dispenser 12 in the device generally includes a support 14 which defines a well 16 dimensioned and sized to receive a quantity of a blood sample, and typically between about 25-50 $\mu$l of blood. A capillary conduit or means 18 formed in the plate is provided at the base of the well and communicates with notched region 20 formed in the upper edge of the support. The construction of the well, tube and notched region in the support can be appreciated from FIGS. 1 and 3. The support is preferably a thin plastic plate or the like, with the well, tube and notched region formed by standard molding or machining methods.

A sieving matrix 22 carried in region 20 functions to partially remove blood cells (including blood cells and other large particulate material in the blood sample) as the sample migrates through the matrix in a bottom-to-top direction in the figures. Specifically, matrix 22 is formed of a fibrous matrix filter material designed to draw aqueous fluid by surface wetting, and to retard the movement of blood cells as the blood sample is drawn through the matrix. That is, the matrix serves as a chromatographic medium for separating cell-size particles from soluble serum components on the basis of different migration rates through the medium.

A variety of fibrous materials, such as are used in fibrous-mat filters, including cellulose, cellulose acetate, and glass fibrous matrices, are suitable materials for matrix. The fibers may be crosslinked, if desired, by chemical crosslinking, heat fusion, or the like. Also suitable are porous substrates, such as sintered glass, fused polymer beads, and the like whose wettability and dimension of interstices are such as to promote movement of an aqueous medium into the matrix by surface wetting. The surface of strip 26 which is in contact with membrane 24 is also referred to herein as the inner surface of the strip, and the opposite strip surface is referred to as the outer strip surface. One exemplary filter is a glass fiber filter having a packing density of about 0.5 gm/cm$^3$, side dimensions of between about 3 mm, and a thickness of about 125 $\mu$. The pad is dimensioned to absorb a defined volume of sample fluid, typically about 3-25 $\mu$l, and preferably between about 15-25 $\mu$l.

The upper surface of matrix 22 is covered by a microporous membrane 24. This membrane is designed to filter out blood cells and other particulate matter present in the fluid sample. Where the device is used for assaying total cholesterol or other lipid components which may be associated with large lipoprotein bodies in the blood, e.g., high density lipoproteins (HDLs), low-density lipoproteins (LDLs), and very-low density lipoproteins (VLDLs), the membrane pore sizes are selected to filter out blood cells, but allow passage of these lipid bodies. One preferred membrane is a polycarbonate membrane available from Nuclepore (Livermore, CA) and having a 1 micron pore size. The membrane is also referred to herein as filter means.

Membrane 24, in turn, is covered by an absorbent strip 26 which is attached to and extends along an interior portion of the plate's upper edge. Strip 26 serves to distribute sample fluid from a central region 28 of the strip, which is contact with matrix 22 through membrane 24, to opposite end regions 30, 32 of the strip, and more particularly, to multiple sample-transfer sites at opposite end regions of the strip, such as sites 34, 36 in end region 30, and sites 38, 40 in end region 32 (FIG. 1). The strip is also referred to herein as a distributing matrix or distributing means for distributing sample from the sieving matrix to multiple sample-transfer sites in the distributing matrix.

Figure 3:
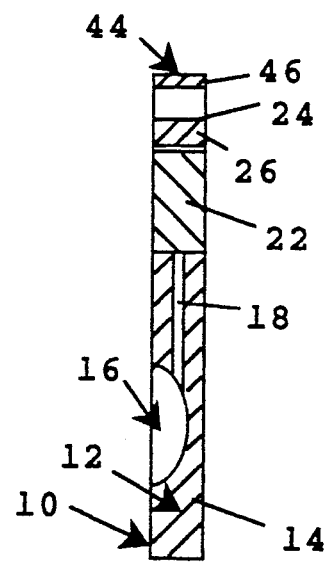
FIG. 3 is a sectional view taken along line 3—3 in FIG. 1.
Figure 4:
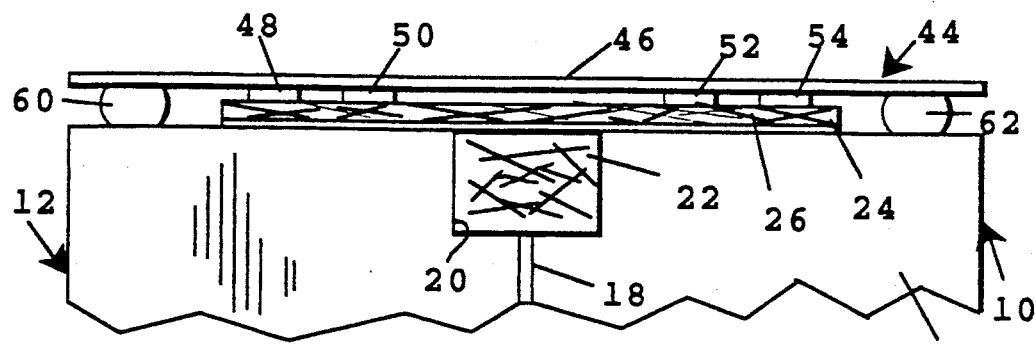
FIG. 4 is a plan view similar to FIG. 1, but showing the sample-delivery device in a sample-delivery position.

Strip 26 preferably has a lower fiber density than the strip, giving greater fluid flow rate through the pad than through the strip. The strip is preferably formed of a fibrous material, such as employed in the sieving matrix, which is capable of drawing fluid through the strip by capillary flow. One exemplary strip material is a glass fiber filter having a packing density of about 0.2 gm/cm$^3$, a thickness of about 125 $\mu$, and a length of about 3 cm. As seen in FIG. 3, the sieving matrix, membrane, and strip all have about the same width dimension as plate 14, typically between 1-5 mm.

In operation, a blood sample, typically 25-40 $\mu$l, is introduced into well 16, from which it is drawn by tube 18 into matrix 22. As the sample is drawn through the matrix by capillary flow, cellular components in the blood are retarded and the leading edge of the blood sample becomes progressively depleted of cell components. The reduced concentration of the blood cells of the sample material which reaches membrane 24 reduces the tendency of the membrane to clog as sample material is drawn though the membrane by capillary flow into strip 26. After passage through membrane 24, the sample is essentially a cell-free plasma fluid which is then drawn toward the sample-transfer regions at the opposite end regions of the strip.

In one alternate embodiment, the filter means for completely removing blood cells from sample at the sample-transfer sites is provided by the distributing matrix or strip itself. Here the sieving and distributing matrices act as a continuous chromatography medium which is effective to completely separate the faster-migrating serum from the slower-migrating blood cell, when the sample first reaches the sample-transfer sites in the dispenser.

In still another embodiment, the filter means is a microporous membrane like membrane 24, but placed over the outer surface of the distributing matrix. Here the sample transfer sites are on the outermost surface of the membrane, corresponding to the opposite end regions of the underlying distributing matrix. As in the above-described embodiments, the filter means here acts to substantially completely remove blood cells and similar-size or larger particulate material in the blood sample as the sample migrates to the sample-distribution sites.

With continued reference to FIGS. 1-4, device 10 includes a test plate 44 composed of an elongate strip 46, and multiple wettable, absorbent test pads 48, 50, 52, and 54 carried on the lower surface of the support, at positions directly above the four corresponding sample-transfer sites 34, 36, 38, and 40 in the dispenser, respectively. That is, the four pads are positioned on the support for contact with the corresponding transfer sites in the dispenser, when the support is moved to a sample-delivery position, described below with respect to FIG. 4. The strip is transparent or has transparent windows which allow the pads to be viewed through the strip.

In the present embodiment, the device includes four sample-transfer sites and four associated pads. More generally, the device includes at least two and up to six or more pads and sample-transfer sites.

The pads in the test plate are attached to the support by a transparent or translucent adhesive material (not shown), or by sonic welding or other suitable bonding method. Each pad contains analyte-dependent reagents effective to produce an analyte-dependent change in the pad which can be detected optically, either visually or by a detector, in a known manner. The nature of the reagents for exemplary analyte assays is given below. Desirably, the reaction pads are porous, fused polymer or microporous polymer membranes having a thickness, after complete penetration of the fluid, of about 100-150 $\mu$ and side dimensions of about 3 mm. Preferred membranes are polysulfone, polypropylene, nylon, nitrocellulose, Teflon TM, or polyvinylchloride microporous membranes having a pore size preferably between about 0.1-10 $\mu$, and preferably 0.3 to 1 $\mu$. Polysulfone membranes are advantageous in that the membrane is relatively opaque when it absorbs a clear fluid sample. The absorption volume of each pad is preferably between about 0.5-2 $\mu l$.

The test plate is mounted on the dispenser by a pair of resilient members, such as elastomeric blocks 60, 62. The blocks act to bias the pads toward a non-transfer position at which the pads are spaced apart from the dispenser's sample-transfer surface, with a spacing typically of between about 0.5 to 1.0 mm.

In operation, when a serum sample reaches the sample-transfer sites in the dispenser, the test plate is moved toward its sample-transfer position (FIG. 4), at which the exposed, confronting surfaces of the pads are in contact with the corresponding transfer sites. At this position, sample fluid in the dispenser is drawn into the pads by capillary flow with fluid movement occurring in a direction normal to the pad surfaces. The plate is held at this position until a desired degree of wetting of the pads is achieved. The degree of wetting may be followed, for example, by the change in opacity of the pads, as viewed from the top, since the generally opaque pads become somewhat translucent as they are wetted. Alternatively, the time required for optimal pad wetting, at a selected contact pressure and pad material and thickness, can be calibrated. The pads are then wet under the selected pressure conditions for the calibrated time.

Figure 5:
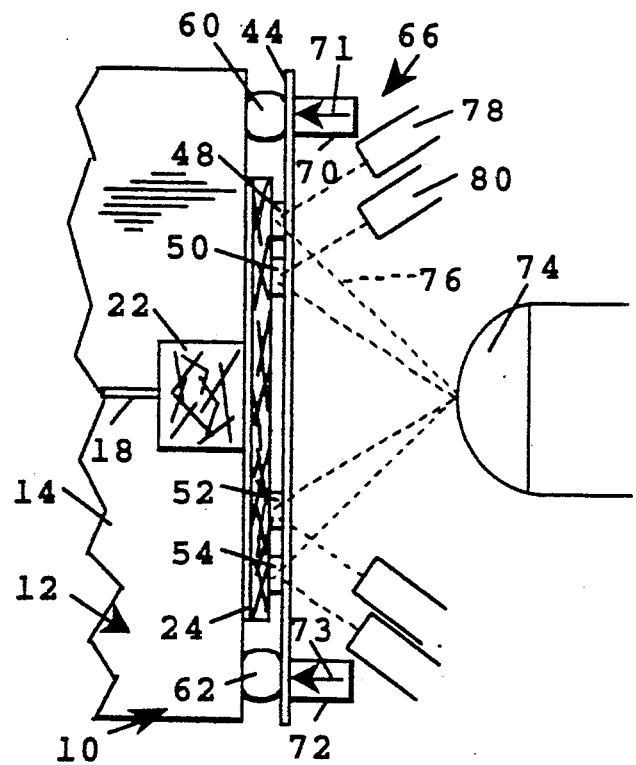
FIG. 5 is partially schematic plan view of the FIG. 1 assay device shown operatively with an assay apparatus designed for quantitating analyte concentration in the assay pads of the device.

One apparatus which is specifically designed for use with the device, for achieving quantitative fluid volume transfer to the test pads, is shown schematically at 66 in FIG. 5. This apparatus has been detailed in above-referenced co-pending U.S. patent application "Controlled-Volume Assay Method and Apparatus."

Briefly, the apparatus includes a light-tight housing (not shown) in which the assay device of the invention is supported. The test plate in the housing is engaged by a pair of solenoid-activated plungers, indicated at 70,72, which are designed to move the test plate to its sample-transfer position when the solenoid is actuated. The plungers are operable to hold the pads simultaneously at their sample-transfer position until released, to deliver a body fluid sample to the lower surface regions of the pads. It is noted that resilient blocks 60, 62, which are compressed during a sample-transfer operation, function to equalize the forces between the sample-transfer surface and each pad.

During sample transfer, the sample in the dispenser will migrate into and through each pad at a rate which causes the pad to become completely wetted over a given sample-transfer time. Typically, in the embodiment described herein, a pad becomes completely wetted within a sample-transfer period of about 1-3 seconds.

Apparatus 66 further includes a light source 74 which produces directed light beams, such as beam 76, which are directed at an angle against each reaction pad, with the sample-transfer device in housing. For each pad, a light detector, such as detectors 78, 80 associated with pads 48, 50, respectively, is provided for monitoring the extent to which the expanse of the pad is wetted during delivery of the sample to the surface region of the pad. More specifically, during sample transfer, as liquid sample migrates into and through a pad, the reflectivity of the surface of the pad will decrease, due to the greater translucency of the pad, which is typically white and relatively reflective in its dry condition. Thus, as the pad is wetted by the migration of liquid sample through the pad, the intensity of the reflectance beam measured by the associated detector until the pad becomes completely wetted. Typically, when reflectance was measured as a function of time after first contact between the pads and dispenser, all of the pads in the test plate showed a sharp decrease in reflectance, over an approximately 2 second time period, after which reflectance plateaus, indicating complete is wetting of the pad. Each pad wetted completely at about the same rate. The detector may be coupled to a microprocessor designed to calculate total sample volume transfer to each pad, as described in the above-mentioned co-pending patent application, Ser. No. 320,474. Once the time required for optimal pad wetting has been measured, or calibrated, the apparatus may be operated for optimal sample-transfer by placing the device in a sample-transfer condition for the calibrated time period.

The detector is also used measure the change in reflectance in the associated pad due to the production of a colored reaction product in the pad, as analyte is utilized in forming the reaction product, after pad wetting occurs. As can be appreciated, when the light beam of the light source has a wavelength at or near the absorption maximum of the colored reaction product, the reflectance from the pad will decrease gradually with continued production of reaction product, until a new (second) reflectance-curve plateau is reached at the end point of the reaction. The total amount of analyte can then be calculated from the difference in reflectance at the first plateau (just after pad wetting) and at the second plateau (at the product end point). Alternatively, the amount of analyte can be calculated from reaction kinetics, based on the rate of change of reflectance observed after pad wetting.

Based on the calculated volume of sample applied to a pad, and the amount of analyte contained in the volume, as determined by an analyte-dependent chemical reaction in the pad, the concentration of analyte in the sample can then be determined by the calculator.

Alternatively, the assay device may be used for qualitative analyte determination, by visual determination of a test pad color intensity. Typically, in this mode, the user applies the blood sample to the dispenser and allows sample to migrate to the sample-transfer sites in the dispenser, as judged visually. The test plate is then moved manually to the sample-transfer position, and held there briefly until the test pads have filled, again as judged visually by the change in translucence of the pads. The final color reaction, from which concentration of analyte is determined, can be measured qualitatively by comparison with known color standards.

B. Multiple Analyte Assays

The assay device of the invention is designed particularly for determination of blood analytes such as lipids, in which a battery of different lipid analytes are part of an overall diagnostic test. In one preferred example, described below, the device is designed for assay of total serum cholesterol and serum triglycerides, and optionally for determination of HDL cholesterol subfraction, such as free and esterified serum cholesterol. In a more general preferred configuration, the device is designed for self-corrected analyte determinations of multiple analytes, as described in co-pending U.S. patent application for "Self-Corrected Assay Device and Method," Ser. No. 369,326, filed Aug. 23, 1989.

In this more general configuration, the test pads each contain common-pathway reagent components for converting $H_2O_2$ to a distinctly colored signal reaction product. The components include peroxidase, and a dye (meaning a single dye or coupled dye system) is converted by the peroxidase, in the presence of $H_2O_2$, to a distinctively colored, signal reaction product. The peroxidase enzyme is a hydrogen-peroxide oxidoreductase, such as horseradish peroxidase, myeloperoxidase, and lactoperoxidase, which catalyses the reaction:

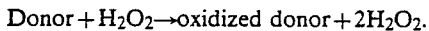

Donor + $H_2O_2 \rightarrow$ oxidized donor + $2H_2O_2$.

The specificity of the enzyme for the donor is generally low, and a number of phenols, aminophenols, diamines, and indolephenols are active. In the present invention, the donor is selected among a variety of known compounds or pairs of compounds which undergo reaction to a detectable, typically chromogenic reaction product as a result of peroxidase-catalyzed oxidation.

Exemplary donor compounds include O-phenylenediamine, amidopyrine, and naphthalene-2,3-dicarboxaldehyde. Typically formation of a colored reaction product involves dimer formation.

In addition to components, the first test pad of the common pathway, which is used as a self-correcting standard, the reagents in the pad also includes a known amount of reference compound which is not present in the blood sample, and an oxidase enzyme effective to generate $H_2O_2$ by reaction with the reference compound. A preferred reference compound is a D-amino acid, and a preferred oxidase, D-amino acid oxidase. The reference compound and oxidase enzymes are preferably contained in separate layers of the test pad, as described in the above-referenced patent application, Ser. No. 238,775.

When sample fluid is introduced into this first pad, the reference compound is brought into solution and into contact with the oxidase enzyme, with the generation of $H_2O_2$ and $H_2O_2$-dependent generation of colored reaction product. The intensity of the colored reaction product will depend (i) the amount of known reference compound in the pad (which is known), (ii) the condition of the enzyme reagents in the pad, including the oxidase enzyme, (iii) the reaction conditions, such as ambient temperature, and (iv) the inhibitory effect of components in the blood sample fluid. It will be appreciated that factors (ii–iv) are applicable to the common-pathway components for color generation from $H_2O_2$ present in each of the test pads, and thus provides a self-correcting standard for each of the other test pads.

The remaining test pads contain reagent components effective to generate $H_2O_2$ by reaction with selected analytes, including an oxidase enzyme which is specific for the selected substrate. Table I shows several exemplary analytes for which suitable analyte-specific oxidases exist. As seen, the analytes may themselves be the substrate of the analyte-specific enzyme, as in the case of glucose, uric acid, amino acid oxidase, and free (non-esterified) cholesterol. Here the analyte-specific oxidase reagents may include only the oxidase enzyme.

Alternatively, the analyte may be first converted by primary analyte-specific enzyme(s) to produce the substrate recognized by the oxidase enzyme. Here the analyte-specific oxidase reagents include both the oxidase and additional enzyme for converting the analyte to the oxidase substrate.

In the case of esterified cholesterol, for example, the analyte-specific oxidase reagents include cholesterol esterase, for converting cholesterol in esterified form to free cholesterol, and cholesterol oxidase, which produces cholestenone and $H_2O_2$ in the presence of oxygen.

The analyte-specific oxidase reagents for determination of serum triglyceride include lipase, which hydrolyses triglyceride to glycerol and free fatty acids; glycerol kinase, which converts glycerol to glycerol-phosphate in the presence of ATP; an ATP-generating system; and glycerol-phosphate oxidase, which reacts with glycerol-3-phosphate to produce dihydroxyacetone-phosphate plus $H_2O_2$.

The analyte-specific oxidase reagents for determination of creatinine include creatinine amidohydrolase, which converts creatinine to urea and sarcosine, and sarcosine oxidase, which converts sarcosine to glycine and formaldehyde, with production of $H_2O_2$.

TABLE I

| Analyte | Substrate | Oxidase |
| --- | --- | --- |
| glucose | glucose | glucose oxidase |
| uric acid | uric acid | uricase |
| amino acid | amino acid | amino acid oxidase |
| free cholesterol | cholesterol | cholesterol oxidase |
| esterified cholesterol | cholesterol | cholesterol oxidase |
| triglyceride | L-glycerol-3-phosphate | L-glycerol-3-phosphate oxidase |
| creatinine | sarcosine | sarcosine oxidase |

One exemplary three-pad device, designed for determination of total serum cholesterol and triglyceride, contains in each pad, in addition to the above common-pathway peroxidase and dye components:

(i) in the first pad, a known amount of a reference compound which is not present in the blood sample, and a reference-compound oxidase effective to generate $H_2O_2$ by reaction with the reference compound, (ii) in the second pad, cholesterol esterase and cholesterol oxidase enzymes, for generating $H_2O_2$ from free and esterified serum cholesterol and (iii) in the third pad, triglyceride hydrolase, L-glycerol kinase, and L-glycerol-3-phosphate oxidase, for generating $H_2O_2$ from triglyceride.

A fourth test pad in the above device may be designed for one of a variety of tests. In one embodiment, the fourth test pad contains the same reagent components as the first pad, but with a different known amount of reference compound. This configuration is used in generating a two-point standard correction curve, as described in the above-referenced patent application, Ser. No. 396,326.

In a second embodiment, the fourth reaction contains the same reagent components as the second pad, except that cholesterol esterase is absent. This pad thus generates $H_2O_2$ from free cholesterol, but not esterified cholesterol, and can be used, in conjunction with the total cholesterol test pad reading, to calculate total esterified cholesterol.

In a third embodiment, the fourth pad contains reagent enzymes, such as glucose oxidase, for assay of other serum components, such as glucose. It will be appreciated that the test device may contain more than three or four test pads, and thus incorporate all of the above variants and/or other analyte tests.

From the foregoing, it can be appreciated how various objects and features of the invention are met. First, the assay device provides accurate analyte determination of multiple blood analytes present from a single drop of whole blood, typically less than 40–50 μl volume. Secondly, the device acts to separate blood cells from blood fluid, to eliminate color and other cell-related interference with the assay. Thirdly, the volume of sample which is transferred to the test pads can be controlled by controlling sample-transfer time.

Several features of the device are important for achieving the above results. The dispenser construction in the device allows for a small blood-sample volume to be distributed to multiple dispenser sites, with removal of blood cells as the sample migrates to the sites. The test plate allows sample fluid to be transferred at a selected transfer time when the volume of sample at each sample transfer site is most nearly equal. That is, sample-transfer can be timed to correspond to the time point when all of the sample transfer sites in the dispenser first filled. Further, where the cell filtering in the device is accomplished entirely by chromatographic separation in the sieving and distributing matrices, sample transfer can be carried out after all of the sample-transfer sites are filled, but before migration of any blood cells into the sites occurs.

The test plate construction, and its interaction with the dispenser, permits controlled volume transfer to the test pads, and for quantitating the amount of volume transferred to the pads. Since the volume transfer occurs across the entire outer surface of the pad, i.e., in a direction normal to the surface of the pads, reagent components in the pad are dissolved uniformly throughout the pad.

In a preferred embodiment of the device, the test pads have common end-reaction reagents which convert an intermediate reaction product, $H_2O_2$, to a detectable product, and at least one of the pads includes a reference compound which utilizes the common reagents. This configuration allows for (i) determination of analyte concentrations based on standard curve and (2) self-consistent correction for errors which may result from loss of activity of the common pathway reaction components, inhibitory effects of the sample on the common-pathway reaction components, and temperature and other reaction-condition effects.

Although the invention has been described with reference to particular embodiments and configurations, it will be appreciated by one skilled in the art that various changes and modifications may be made without departing from the invention.

It is claimed:

1. An assay device for use in assaying multiple analytes in a blood sample whose volume is no more than about 50 μl, comprising a sample dispenser having (i) a support, (ii) a well defined in the support for receiving such sample, (iii) a sieving matrix on said support effective to selectively retard blood cells when a blood sample is applied to one end of the matrix as the sample migrates by capillarity toward the opposite matrix end, (iv) capillary means for drawing sample fluid from said well into the matrix, and (v) an absorbent strip on said support having a central region in fluid contact with said opposite matrix end for distributing sample fluid from the sieving matrix by capillary flow to sample-transfer sites in opposite end regions of the strip, a test plate carrying a plurality of wettable, absorbent pads, each having an exposed outer surface region and a defined expanse, said plurality of pads containing reagent means effective to produce a detectable analyte-dependent reaction product for detection of a selected analyte, when sample fluid is transferred from said associated sample-transfer sites to said plurality of pads, and means mounting said plate on said dispenser, said mounting means being adjacent to and spaced from said plurality of pads, for movement toward and away from a sample-transfer position at which substantially the entire outer exposed surface regions of said plurality of pads are in contact with the sample-transfer sites, for simultaneous transfer of substantially the same volume of sample fluid from each of said transfer sites to each of said plurality of pads in the support with fluid movement at a substantially uniform flow rate in a direction normal to the pad outer surface regions throughout the entire expanse of each pad, whereby said plurality of pads are filled uniformly to a selected volume when said plurality of pads are held in contact with said sample-transfer sites for a selected period of time.

2. The assay device of claim 1, wherein said sieving matrix is a glass fiber matrix dimensioned to absorb a blood volume of less than about 25 μl.

3. The assay device of claim 2, wherein said absorbent strip is a glass fiber matrix strip dimensioned to absorb a sample volume of less than about 25 μl.

4. The assay device of claim 1, which further includes a microporous membrane interposed between and in contact with said sieving matrix and strip.

5. The device of claim 1, wherein said plurality of pads are microporous polymer substrate membranes each having a pore size of between about 0.3 and 1.0 microns, and an absorption volume of between about 0.5 to 2 μl.

6. The device of claim 5, wherein said plurality of pads are polysulfone membranes.

7. The device of claim 1, wherein said mounting means includes biasing means for biasing said plate away from its sample-transfer position.

8. The device of claim 1, for use in assaying serum cholesterol and lipoproteins, wherein said plurality of pads comprises first, second, and third pads, the reagent means in each pad includes a peroxidase and a dye which is converted in the presence of $H_2O_2$ to a distinctly colored signal reaction product, and the reagent means in said plurality of pads further includes:
  (i) in the first pad, a known amount of a reference compound which is not present in the blood sample, and a reference-compound oxidase effective to generate $H_2O_2$ by reaction with the reference compound,
  (ii) in the second pad, cholesterol esterase and cholesterol oxidase enzymes, and
  (iii) in the third pad, triglyceride hydrolase, L-glycerol kinase, and L-glycerol-3-phosphate oxidase.

9. The device of claim 8, wherein said reference compound is a D-amino acid, and the reference-compound oxidase is D-amino acid oxidase.

10. The device of claim 8, additionally for use in assaying free and esterified serum cholesterol, wherein said plurality of pads includes a fourth pad whose reagent means includes the same reagent components as the second pad except for cholesterol esterase, which is absent in the fourth pad.

11. The device of claim 8, additionally for use in assaying serum glucose, wherein said plurality of pads includes a fourth pad whose reagent means includes glucose oxidase, said peroxidase, and said dye.

12. The device of claim 8, wherein said plurality of pads includes a fourth pad whose reagent means is the same as that of the first pad, except that the fourth pad contains a different known amount of reference compound.

13. An assay device for use in assaying multiple analytes in a blood sample whose volume is no more than about 50 μl, comprising
  a sample dispenser having (i) a support, (ii) a well defined in the support for receiving such sample, (iii) a sieving matrix on said support effective to selectively retard the movement of blood cells, as a blood sample is drawn by capillary flow from one end of the matrix to the other end, said element having a total absorption volume of less than about 25 μl and a surface area between about 5 and 15 mm$^2$, (iv) capillary means for drawing sample fluid from said well into the matrix (v) an elongate fibrous matrix strip having inner and outer surfaces, and a central region in fluid contact, at the inner strip surface, with said opposite matrix end effective to draw blood sample fluid supplied to a central region of the strip from the matrix by capillary flow toward sample-transfer sites in opposite end regions of the outer strip surface, said strip having a total absorption volume of less than about 15 μl and a total strip area of between about 50-150 mm$^2$,
  a test plate carrying a plurality of wettable, absorbent pads, each having an exposed outer surface region, a defined expanse, a total absorption volume of between about 0.5-2 μl, and reagent means effective to produce a detectable analyte-dependent reaction product for detection of a selected analyte, when sample fluid is transferred from said associated sample-transfer sites to said plurality of pads, and
  means mounting said plate on said dispenser, said mounting means being adjacent to and spaced from said plurality of pads, for movement toward and away from a sample-transfer position at which substantially the entire outer exposed surface regions of said plurality of pads are in contact with associated sample-transfer sites for simultaneous transfer of substantially the same volume of sample fluid from each of said transfer-sites to each of the pads in the support with fluid movement at a substantially uniform flow rate in a direction normal to said plurality of pads outer surface regions throughout the entire expanse of each pad, whereby said plurality of pads are filled uniformly to a selected volume when said pads are held in contact with said sample-transfer sites for a selected period of time.

14. The assay device of claim 13, for use in assaying serum cholesterol and lipoproteins, wherein said plurality of pads comprises first, second, and third pads, the reagent means in each pad includes a peroxidase and a dye which is converted in the presence of $H_2O_2$ to a distinctly colored signal reaction product, and the reagent means in said plurality of pads further includes:
  (i) in the first pad, a known amount of a reference compound which is not present in the blood sample, and a reference-compound oxidase effective to generate $H_2O_2$ by reaction with the reference compound,
  (ii) in the second pad, cholesterol esterase and cholesterol oxidase enzymes, and
  (iii) in the third pad, triglyceride hydrolase, L-glycerol kinase, and L-glycerol-3-phosphate oxidase.

15. The device of claim 14, wherein said reference compound is a D-amino acid, and the reference-compound oxidase is D-amino acid oxidase.

16. The device of claim 14, additionally for use in assaying free and esterified serum cholesterol, wherein said Plurality of pads includes a fourth pad whose reagent means includes the same reagent components as the second pad except for cholesterol esterase, which is absent in the fourth pad.

* * * * *